United States Patent [19]

Shen et al.

[11] Patent Number: 5,263,860
[45] Date of Patent: Nov. 23, 1993

[54] ASEPTIC HOSE CONNECTOR AND CAP

[76] Inventors: James Shen; Rily Young, both of 18751 Beach Blvd., Huntington Beach, Calif. 92648

[21] Appl. No.: 919,861

[22] Filed: Jul. 27, 1992

[51] Int. Cl.⁵ .................. A61C 17/06; A61C 17/14; A47L 9/02
[52] U.S. Cl. .................................. 433/91; 15/422
[58] Field of Search .............. 433/91, 95, 96, 116; 15/419, 422

[56] References Cited

U.S. PATENT DOCUMENTS

| | | | |
|---|---|---|---|
| 950,109 | 2/1910 | Levkowicz | 433/91 |
| 1,651,894 | 12/1927 | Kent et al. | 15/419 |
| 1,821,451 | 9/1931 | Terry | 433/116 |
| 2,930,069 | 3/1960 | Kowalewski | 15/419 X |
| 3,476,144 | 11/1969 | Krantz | 433/95 X |
| 4,476,607 | 10/1984 | Ross | 15/422 X |
| 4,723,912 | 2/1988 | Nieusma | 433/116 |
| 4,859,182 | 8/1989 | Nerli | 433/116 X |
| 4,872,837 | 10/1989 | Issalene et al. | 433/91 X |

*Primary Examiner*—John J. Wilson
*Assistant Examiner*—Nicholas D. Lucchesi
*Attorney, Agent, or Firm*—David Pressman

[57] ABSTRACT

A connector (12' or 12") is attached to the end of a dental vacuum hose (20) for enabling a valved handle (24) to be attached to the connector and thus coupled to the vacuum hose. A saliva ejector or a high-volume ejector can then be attached to the distal end of the valved handle. The end of the connector is closed with a crown cap (22) to prevent a vacuum rushing sound and keep the connector sanitary when the valved handle is not attached. The cap has a top spike or finial (22F) which enables the cap to be pried off the connector easily by pushing the lumen at the bottom of the valved handle over the finial and tilting the handle. The cap hangs by a tether (22T) after it is pried off. In lieu of a cap, a flip top (12"F) which is hinged to the top opening of the connector can be used; one side of the flip top can be pried with the bottom of the valved handle. Since the crown cap or the flip top can be removed with only one hand holding the handle, the dental professional does not have to touch the connector, thus avoiding soiling it with microorganisms and thereby avoiding the need for many awkward sanitary measures, such as sterilization of the connector and hose, use of plastic shields, etc.

7 Claims, 6 Drawing Sheets

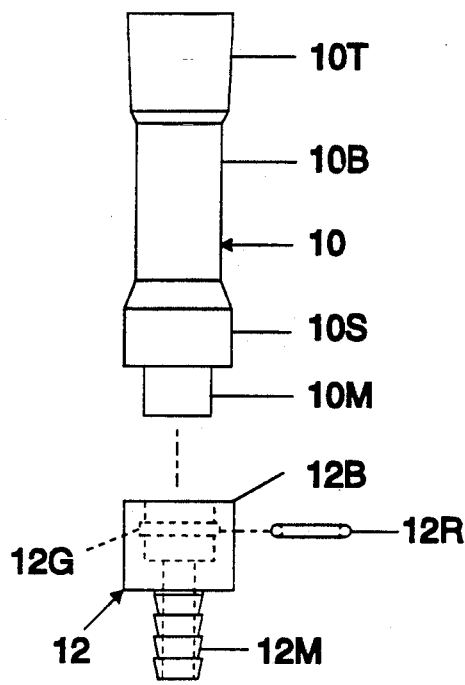
FIG. 1 PRIOR-ART
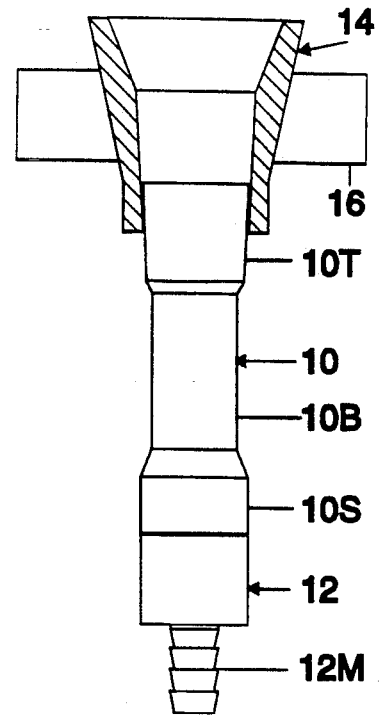
FIG. 1A PRIOR-ART
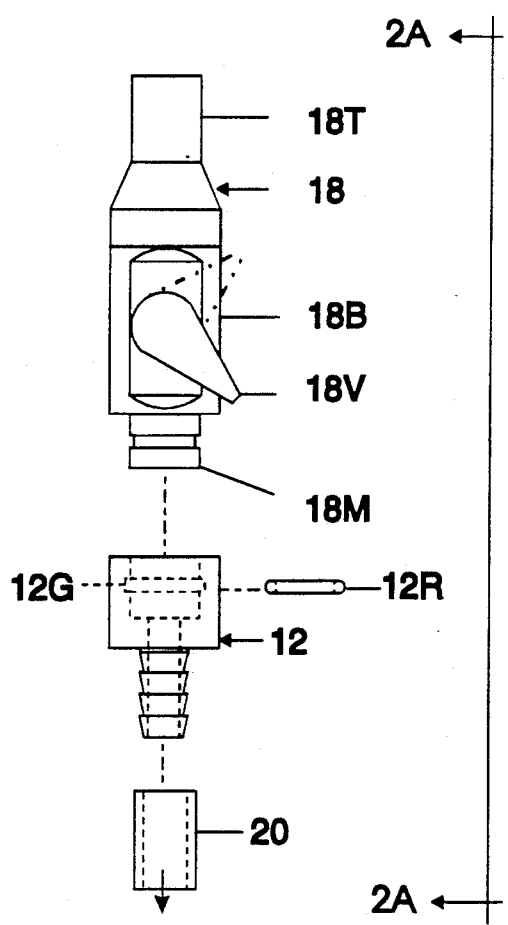
FIG. 2 PRIOR-ART
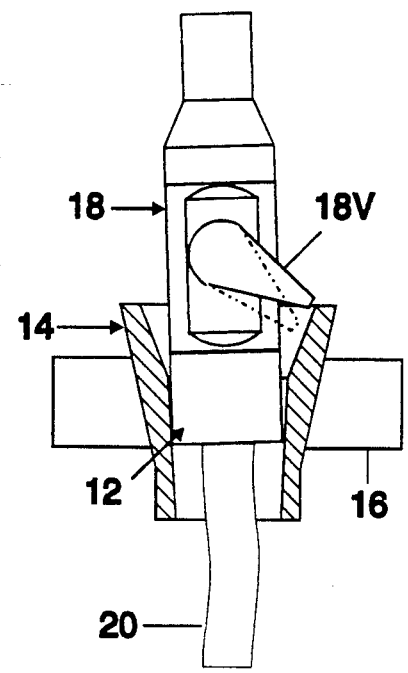
FIG. 2A PRIOR-ART

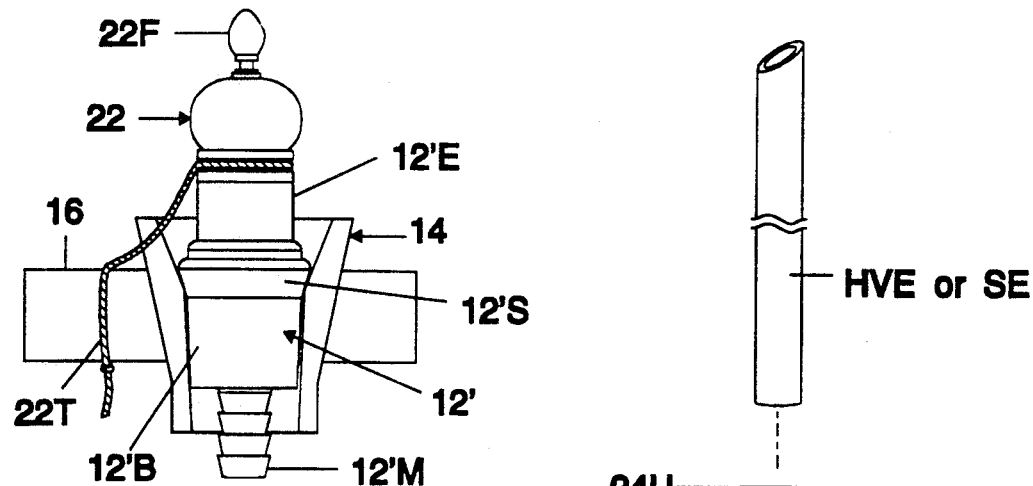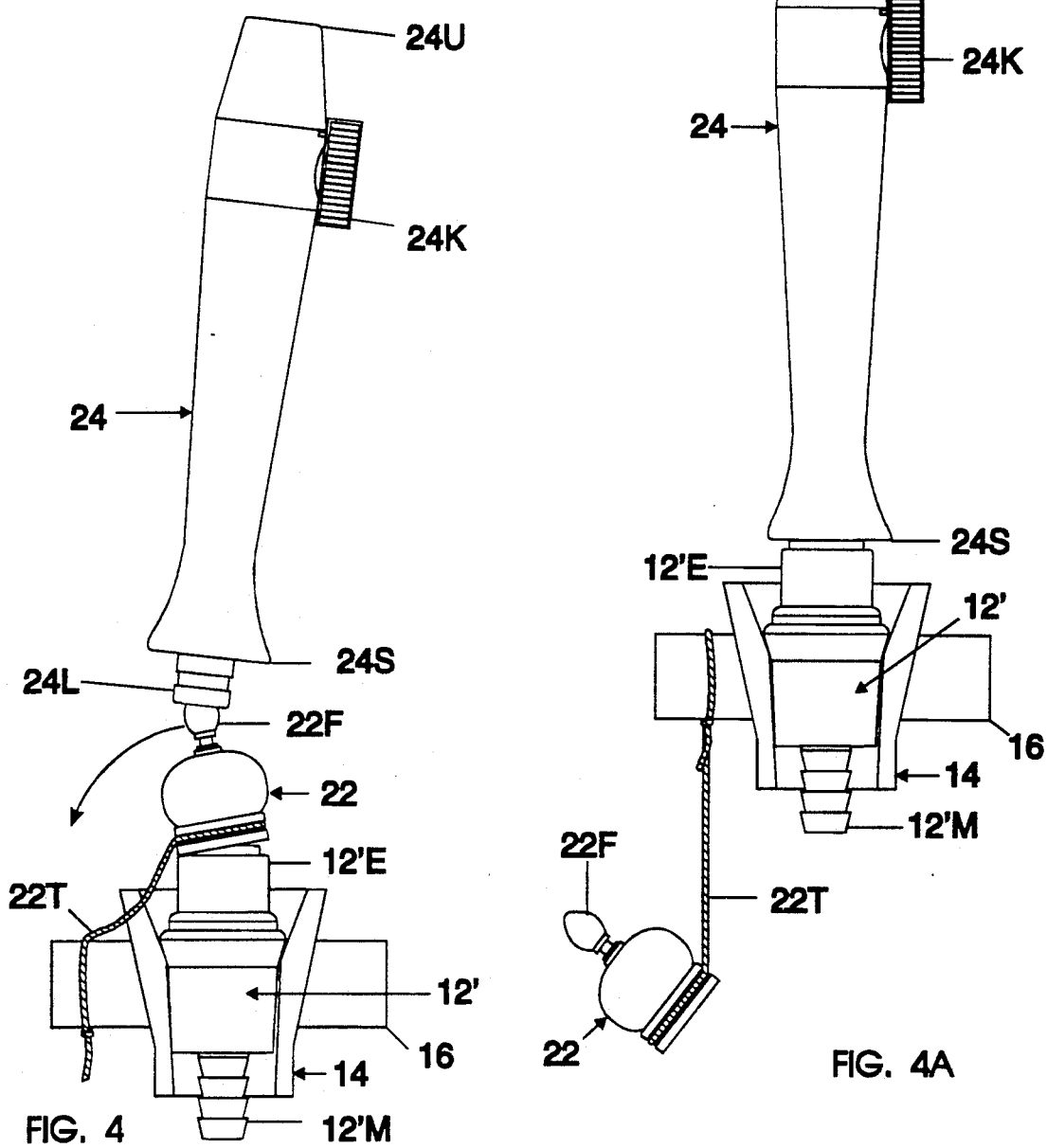

ASEPTIC HOSE CONNECTOR AND CAP

BACKGROUND—CROSS-REFERENCE TO RELATED APPLICATION

The invention of this application is related to that of our copending application, Ser. No. 07/592,360, filed Oct. 3, 1990.

BACKGROUND—FIELD OF INVENTION

This invention relates generally to dental instruments, specifically to improvements in such instruments for minimizing transmission of microorganisms.

BACKGROUND—PRIOR ART

Despite the precautions and measures taken by dentists to keep their instruments sterile, many of their practices and instruments allow undesired MicroOrganisms (MOs), including viruses, bacteria, and fungi, to enter patients' mouths. These MOs generally come from other patients and are known as cross-contaminants since they travel across from one patient to another. They usually make the inter-patient trip via dental instruments, their hoses, and their hose connectors, as will be shortly discussed. Cross-contamination was most undesirable in the past because it spread infectious diseases, such as influenza, colds, hepatitis, etc. However it is extremely undesirable now because of its ability to spread the human immunodeficiency virus (HIV), the eitologic agent of the lethal AIDS disease.

FIG. 1—PRIOR-ART CONNECTOR AND PLUG

In order to understand one modality of cross-contamination, refer to FIG. 1, a perspective view of a prior-art vacuum closure plug 10 (made of plastic) and hose connector 12 which are common to all dental instrument stations. A male lower end 12M of connector 12 has ridges and fits into a vacuum hose (not shown). Its upper end or body 12B comprises a female receptacle with an O-ring groove 12G which holds an O-ring 12R so as to sealingly mate with the lower, male end 10M of plug 10. Male end 10M of plug 10 is pushed into receptacle 12B until the lower shoulder of its stop portion 10S limits its travel. Plug 10 has a body or stem portion 10B and an top grasping portion 10T. The purpose of plug 10 is to close off the open end of hose connector 12 so that dental professionals (dentists and hygienists—DPs) and their patients will not hear any loud rushing sound due to the vacuum applied to the connector from the vacuum hose.

To vacuum debris and saliva from the patient's mouth, the DP first removes plug 10 from connector 12 and then plugs an SE (Saliva Ejector) or HVE (High-Volume Evacuator) valve 18 (FIGS. 2 and 2A) into connector 12. This is disadvantageous for the following reasons:

(1) When the DP removes plug 10 from connector 12, the DP must place it on a countertop where it is free to roll or fall off to the floor, thus contaminating the countertop or any other surface, even if shielded, upon which the plug is placed. Also the countertop or floor will contaminate the plug with dirt or MOs.

(2) The DP must use two hands to remove plug 10 from connector 12—one hand to hold plug 10 and the other to hold connector 12, an awkward, time-consuming operation.

(3) Then the DP must remove the soiled gloves and don new gloves before grasping the sterile SE or HVE, another awkward, time-consuming, and wasteful operation.

(4) When the DP finishes treating the patient, the DP must remove valve 18 from connector 12, another awkward, two-handed, time-consuming operation.

(5) Also the DP's gloved hands are now contaminated from treating the patient, so that connector 12 will be contaminated when the DP grasps it. After the DP replugs connector 12 and later removes the plug and inserts a new valve, the DP will be wearing new gloves, but the soiled connector will contaminate these gloves, so that when the DP inserts any fingers into the next patient's mouth, the DP will transfer MOs from the previous patient to the new patient.

(6) Several governmental disease control and prevention agencies and other infection control experts recommend that DPs use plastic barriers to cover SE and HVE valves, hose connectors and hoses, and many other components and instruments when these are in use. These barriers are expensive, time-consuming to use, and difficult to stock and handle since they come in many shapes and sizes. E.g., there are large plastic covers to cover instrument holders, elongated covers to cover hoses, short covers to cover the SE and HVE valves, etc.

After treating the patient the DP discards the usual rubber (latex) hand gloves and disposable tubes, including the SE or HVE, thereby eliminating any MOs that were deposited on these parts. However these procedures do not affect the MOs that were deposited on the hose, connector 12, and the instrument holders. These MOs are especially difficult to eliminate because the hose has corrugations and many of them are deposited in these corrugations. Hoses with smooth surfaces are now available, but scratches and cracks on their surfaces trap and hold MOs. Since the hose is made of rubber and/or fiber, it is not possible to sterilize it by heat. While it is possible to chemically sterilize it, it is not practical to do so because chemical sterilization takes about 8 to 10 hours and the hose cannot be kept out of service that long. Similarly, it is not practicable to sterilize the instrument holders since these are permanently mounted on the dentist's stand. While heat sterilizable hoses and instrument holders have recently become available, it is awkward to autoclave hoses because they are about two meters long and it is time-consuming and difficult to remove and autoclave hoses and holders after each patient. It is not practicable to sterilize connector 12 since its attachment to hose 12 is semi-permanent and difficult to separate.

Also plug 10 becomes contaminated, necessitating sterilization and the purchase of duplicate plugs so that one can use a sterile one while sterilizing the soiled ones.

As a result, many disease-causing, and even lethal, infections are transmitted between patients with current dental practices, even though DP take many precautions, such as using disposable gloves, disposable ejectors, and plastic instrument and component covers.

FIG. 2—ASSEMBLY WITH SE VALVE

Additional difficulties occur when the DP inserts SE valve assembly 18 (FIG. 2) in place of plain plug 10 (FIG. 1). As shown in FIG. 2, SE valve assembly 18 comprises a body portion 18B having a valve lever 18V for rendering the through lumen of body 18B non-transmissive of fluids therethrough. Valve lever 18V is shown in its full off position in solid lines and in its fully on or transmissive position in phantom lines. The upper end of assembly 18 comprises a rubber cone tip 18T to which a disposable SE (not shown) is connected. The lower end comprises a male connector 18M which plugs into hose connector 12, which in turn is attached to a vacuum hose 20. Male connector 18M has a groove for secure engagement with O-ring 12R. FIG. 2A shows a view of the components assembled and hanging in a universal holder 14.

As shown in FIG. 2A, when the assembly is placed in holder 14, lever 18V will strike holder 14, causing it to rotate partially from its fully closed position (phantom lines) to a partially open position (solid lines). This is undesirable and annoying to the DP and the patient because they will hear a rushing sound due to air entering the assembly. Also, if the holder was not covered by a plastic barrier, MOs will be deposited onto holder 14 from lever 18V and then transferred to the next patient, even though valve 18 is replaced between patients.

OBJECTS AND ADVANTAGES

Accordingly, several objects and advantages of the invention are to provide a way to prevent MOs from one dental patient's mouth from traveling to and entering other patients' mouths; to reduce the spread of infectious diseases, including hepatitis and the AIDS virus, in dental environments; to prevent cross-contamination of dental patients by MOs; to prevent MOs from cross-contaminating patients via dental instruments, their holders, and/or the hands of dental personnel; to avoid the need to chemically or thermally sterilize dental fluid hoses; to prevent such cross-contamination with dental ejectors, evacuators; etc.; to provide a viable alternative to all non-sterilizable instrument holders; to prevent the rushing sound which occurs when a suction tube and valve or connector are removed from a vacuum hose; to avoid the need to turn off the vacuum at its source or the hose valve during this operation; to avoid the need to turn on the valve or source again after a new valve is installed; to avoid any delay associated with the re-turn-on of the source; to avoid the need to sterilize hose connector plugs and provide duplicate plugs for use while one is being sterilized, to avoid loss of such plugs, and to avoid the need to use plastic covers and barriers to cover instruments and parts when in use.

Other objects are to provide dental suction tubes and instruments which can be assembled with one hand and without the use of two hands, thereby to further reduce soiling of vacuum hoses with MOs from the patient's mouth; and to provide a new, attractive, and easy-to-use cap for a vacuum hose connector.

Further objects and advantages will become apparent from a consideration of the ensuing description and the accompanying drawings.

DRAWING FIGS

FIG. 1 is an exploded view of a prior-art plug and vacuum hose connector. FIG. 1A is an assembled view of the components of FIG. 1, hanging from an instrument holder.

FIG. 2 is an exploded view of a prior-art hose, connector, and SE valve assembly. FIG. 2A is a view of the components of FIG. 2 hanging from an instrument holder.

FIG. 3 is an elevational view of a crown cap and hose connector in accordance with the invention mounted in an instrument stand.

FIG. 4 is a view of the components of FIG. 3, plus a valve handle in the process of removing the crown cap. FIG. 4A shows the crown cap removed and the valve handle attached to the hose connector.

Figure 7:
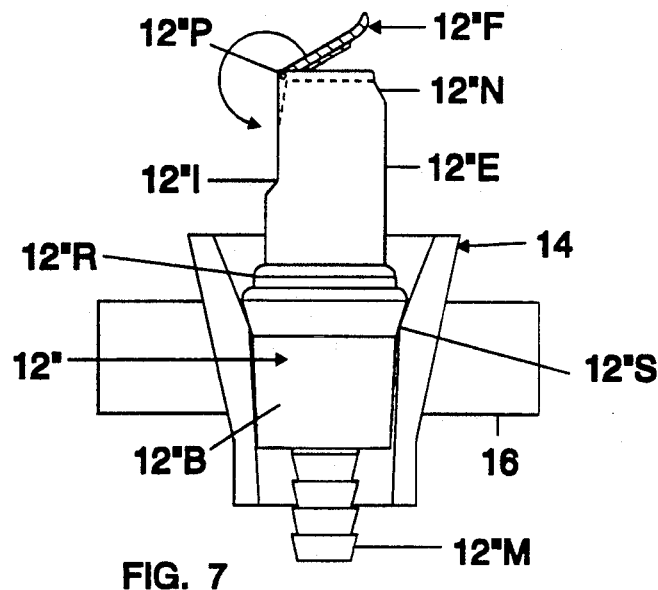
Figure 7A:
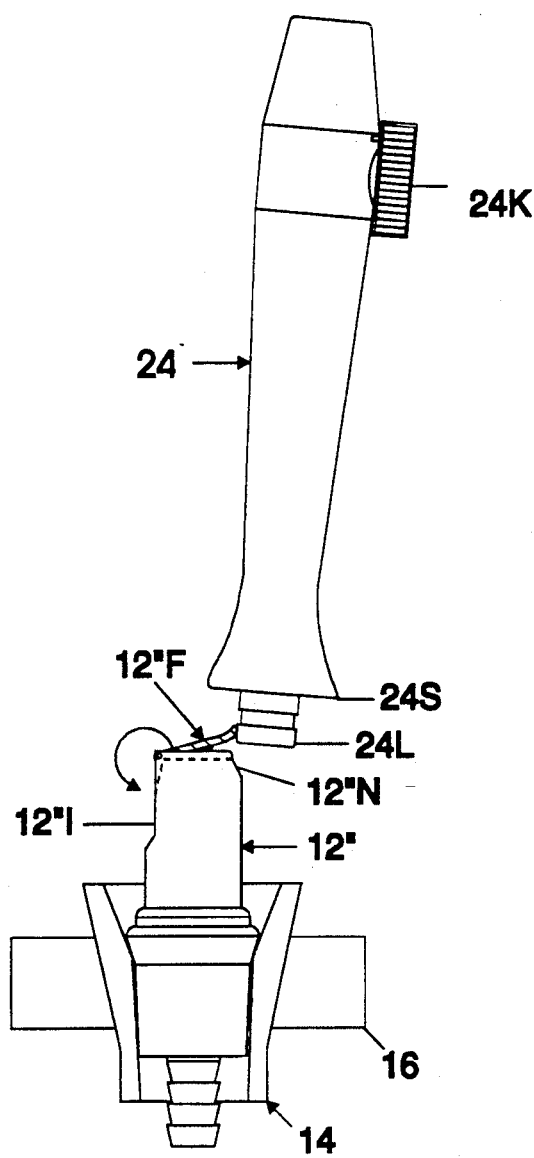
Figure 7B:
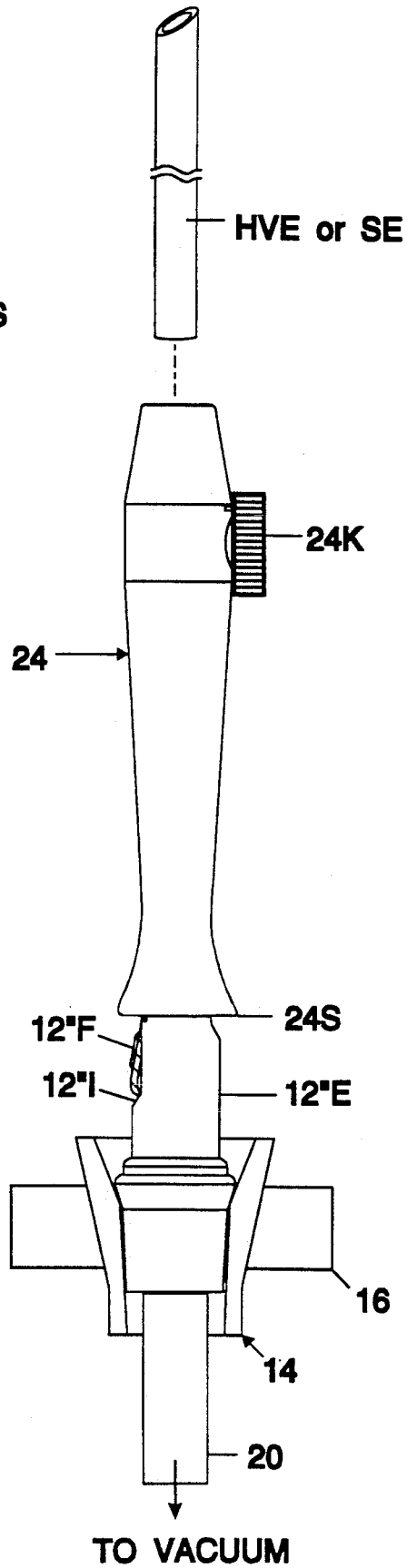
Figure 7C:
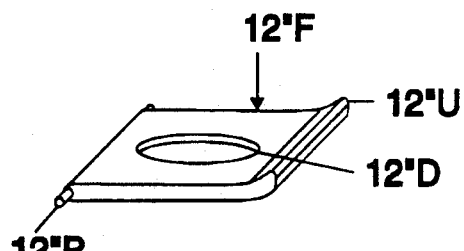
Figure 7F:
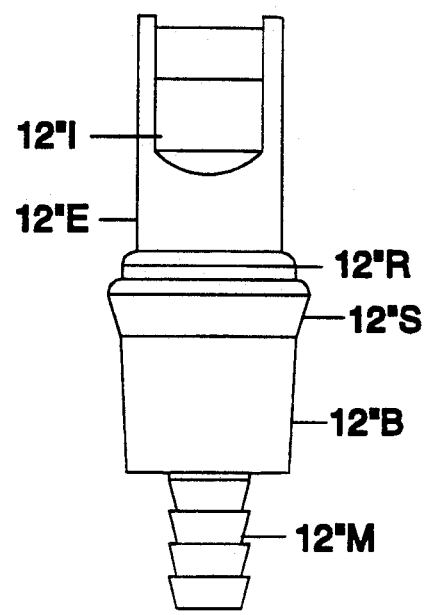
Figure 7D:
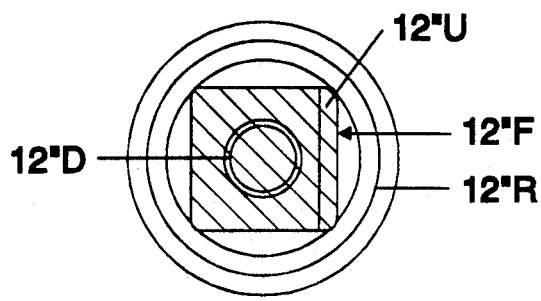
Figure 7E:
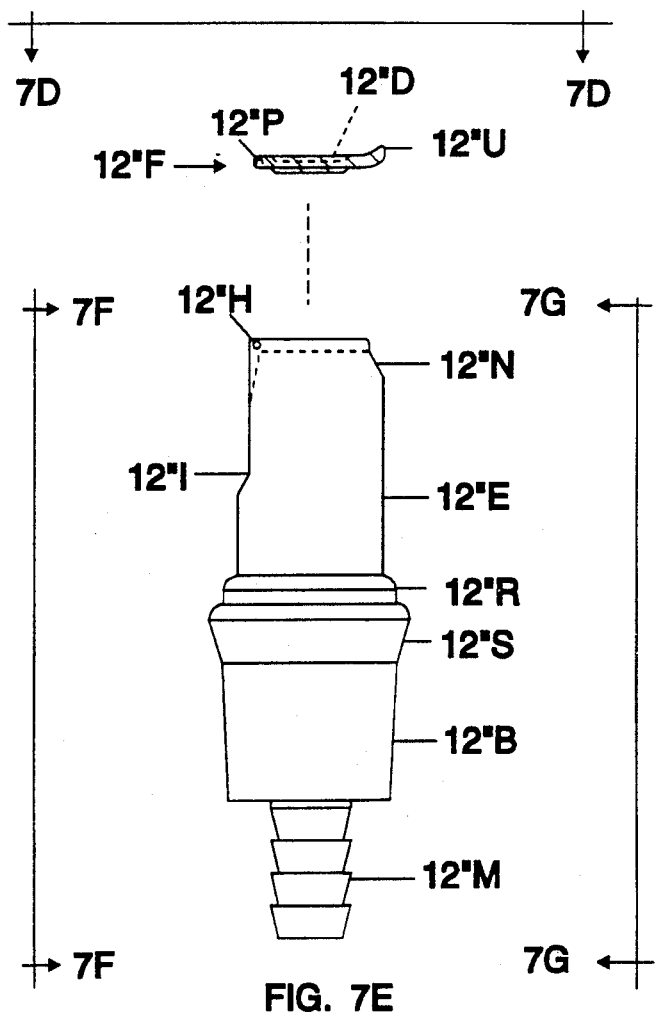
Figure 7G:
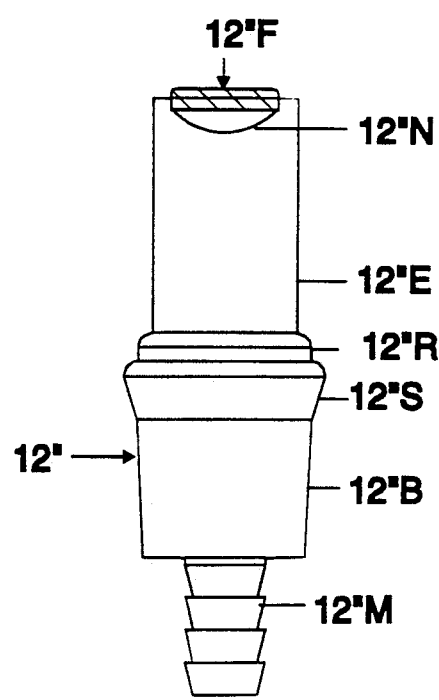

FIG. 7 is an elevational view of a flip-top cap, hose connector, and instrument rest in accordance with another embodiment of the invention. FIG. 7A is a view similar to FIG. 4 but with a valve handle being used to open the cap. FIG. 7B is a view similar to FIG. 4A but with the valve handle connected after opening the cap. FIG. 7C is a perspective view of the cap. FIG. 7D is a top view of the seated cap and hose connector taken in the direction indicated by lines 7D—7D of FIG. 7E. FIG. 7E is an exploded view of the hose connector and the cap. FIG. 7F is a side view of the connector of FIG. 7E taken in the direction indicated by line 7F—7F. FIG. 7G is a side view of the connector of FIG. 7E taken in the direction indicated by line 7G—7G.

Drawing Reference Numerals

| | |
|---|---|
| 10 plug | 10M male end of 10 |
| 10S stop portion | 10B handle portion |
| 10T receptacle portion | 12 prior-art hose connector |
| 12B body | 12R O-ring |
| 12' modified hose connector | 12'E extension at top |
| 12'M male lower end of 12' | 12'B body |
| 12'L lumen | 12G O-ring groove |
| 12'O O-ring | 12'R ridges |
| 12'S shoulder | 12'T male top extension |
| 12" connector for flip top | 12"B body portion |
| 12"D depression | 12"E extension at top |
| 12"F flip-top lid | 12"H hinge pin holes |
| 12"I indentation | 12"M male lower end |
| 12"'N notch | 12"P pins of hinge |
| 12"'R ridges | 12"S shoulder |
| 12"U upturned lip | 14 universal holder |
| 16 bar on instrument stand | 18 SE or HVE valve |
| 18B body portion | 18V valve lever |
| 18T rubber cone tip | 18M male connector |
| 20 vacuum hose | 22 crown cap |
| 22T tether | 22F finial |
| 22R recess | 24 valve handle |
| 24B bore of 24 | 24C cylinder of barrel valve |
| 24K knob of 24 | 24L lower end of 24 |
| 24O O-ring of 24 | 24P pin on 24K |
| 24S shoulder of 24 | 24U upper part of bore |

Abbreviations
HVE High-Volume Evacuator
DP Dental Professional
SE Saliva Ejector
MO microorganism

FIGS. 3, 4, AND 4A—CROWN CAP ATTACHED TO CONNECTOR

In accordance with a first embodiment of the invention, we have substantially overcome the problem of cross-contamination of dental patients by MOs, discussed above in connection with FIGS. 1 and 2, by providing a novel cap for the hose connector, together with means for removing the cap without touching it or the connector and attaching a valved handle without touching the connector or the hose.

As shown in FIG. 3, a modified hose connector 12' rests in conventional instrument holder 14. A vacuum hose (not shown) is normally attached to lower end 12'M of connector 12'. The top of connector 12' is capped and sealed by a novel crown cap 22 which is tethered to instrument holder support bar 16 by a tether line 22T. Cap 22 is a cylindrical dome-shaped member with a circular shape when seen in a top plan view (not shown). It has a graceful, turban-like shape and is convex when seen from the top and concave from the bottom, which is open. It has a spike or finial 22F on its top. Finial 22F extends upwardly and has a pointed tip, a wide body, and a narrow neck portion adjacent cap 22.

Connector 12' has a lower end 12'M which is connected to the vacuum hose (not shown), a body section 12'B, a shoulder 12'S with an inwardly and downwardly tapering surface for mating with holder 14, and a top extension 12'E which is joined to shoulder 12'S by a plurality of external, circumferential rings. Top extension 12'E contains an internal groove which holds an O-ring 12'O (FIG. 5) and a male top extension 12'T which is designed to mate loosely with recess 22R in crown cap 22. Extension 12'E has sufficient length so that top extension 12'T will be above the top rim of holder 14 when the connector rests in the holder. Thus when handle 24 is mated with connector 12', its shoulder 24S will not touch holder 14 in any way.

A valved handle 24 (FIGS. 4 and 4A) is used to remove cap 22 without the DP's hands touching it, as will be explained. Thereafter handle 24 can be connected to connector 12' without the DP's hands touching connector 12'. Handle 24 is a vacuum instrument which comprises an elongated tubular body with a circular, knurled valve knob 24K near its upper end. Knob 24K operates an internal valve in valve handle 24 which renders a lumen (not shown) inside handle 24 transmissive or occluding. The lower end of handle 24 comprises a tubular extension 24L whose internal bore or lumen is sized to fit loosely over part of finial 22F. The external diameter of extension 24L is designed to sealingly mate with the bore of connector 12'. Extension 24L has a circumferential groove for mating with an O-ring within top extension 12'E of connector 12'. The upper end of handle 24 has a bore for receiving and mating with an SE or a HVE tube (FIGS. 4A and 7B).

At its widest part crown cap is about 19 mm in diameter and the other parts are size proportionately. Cap 22 and connector 12' preferably are made of aluminum. Tether 22T is preferably made of nylon or it can be a beaded chain or any other suitable flexible tether, about 20 cm long. It is looped around and attached to bar 16 and a groove around the lower end of cap 22 by welding it to itself or with a cinch band, or by any other suitable method.

Figure 5:
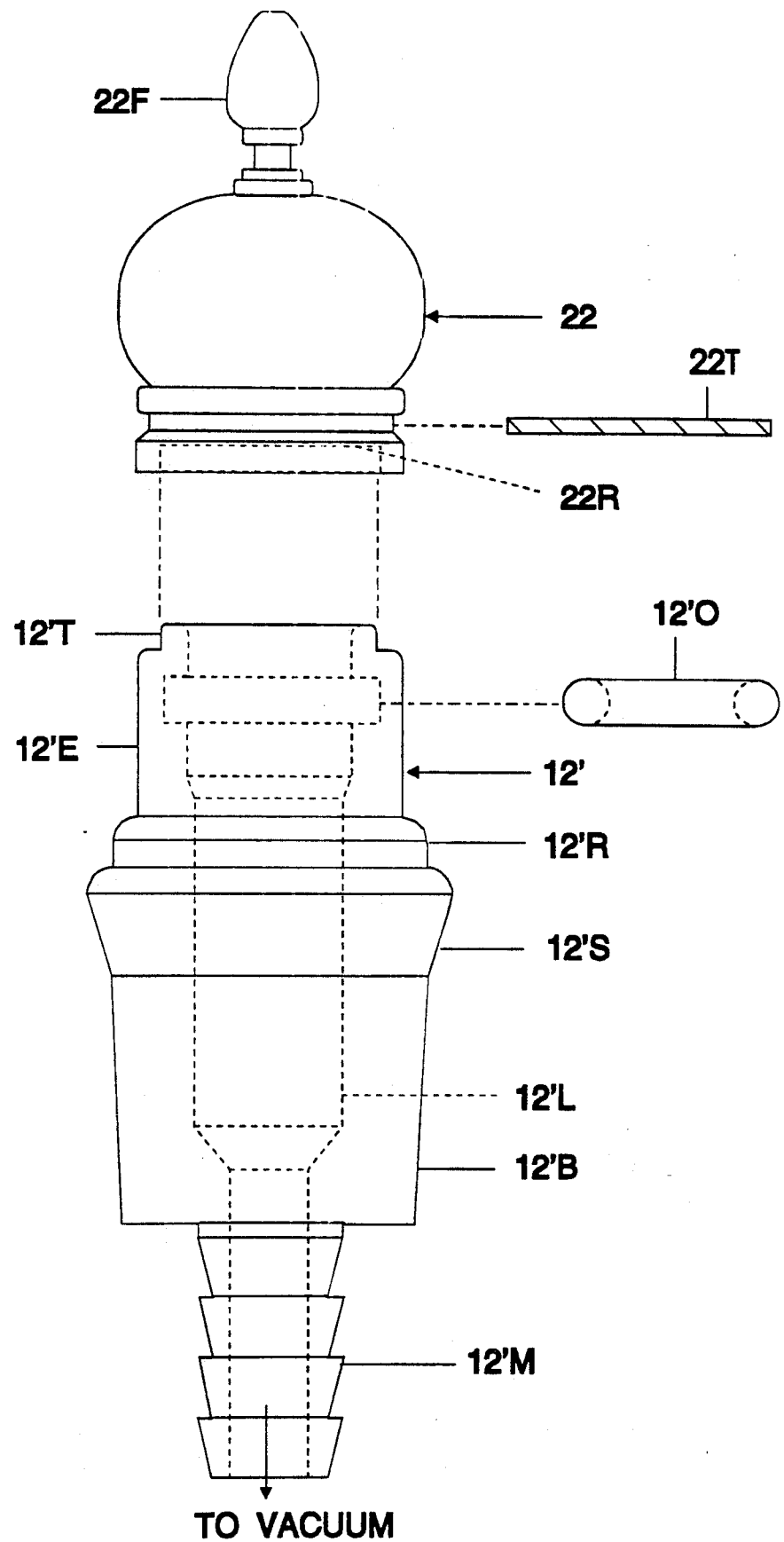
FIG. 5 is an exploded view of the crown cap and hose connector.

FIG. 5—Details Of Crown Cap And Hose Connector

FIG. 5 shows further details of crown cap 22 with tether 22T separated. The bottom of the cap has a recess or female socket 22R which mates with a boss or male upper end of connector 12'. Recess 22R is purposely kept shallow so that it will be easy to remove. A long attachment surface is not needed anyway since the vacuum will hold the cap to the connector. The bore or lumen 12'L of connector 12' provides a female mating receptacle which is designed to receive lower end 24L (FIG. 4) of valve handle 24. End 24L has a circumferential groove and bore 12'L includes an O-ring 12'O (shown exploded away in FIG. 5) to sealingly mate with this groove. Other details of the cap and connector are as shown and need not be detailed.

FIG. 6—DETAILS OF VALVED HANDLE

Figure 6:
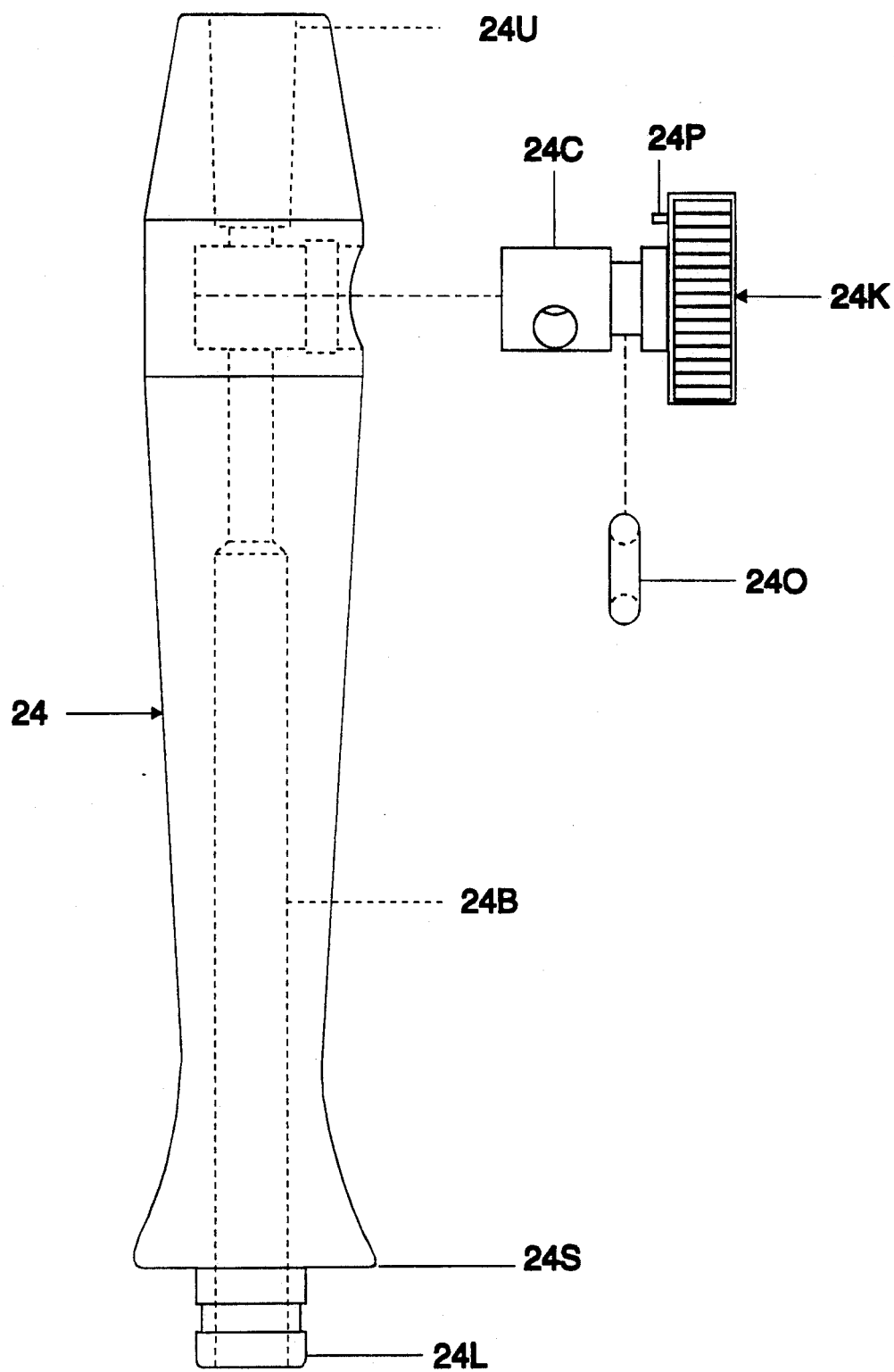
FIG. 6 is an exploded view of the valve handle.

FIG. 6 shows details of valve handle 24. Its lower end 24L comprises a male connector with a groove for mating with the O-ring in hose connector 12'. Insertion of valve handle 24 into the hose connector is limited by a downwardly facing shoulder or skirt 24S above lower end 24L. A bore 24B or lumen runs through handle 24; the part of bore 24B in lower end 24L is dimensioned to fit loosely over part of finial 22F so that handle 24 also serves as a tool which can be held with one hand and used to remove the crown cap. Knob 24K operates a conventional barrel valve cylinder 24C which can occlude bore 24B or allow the bore to be transmissive, depending upon the angular position of the knob. The knob includes a pin 24P and a mating groove with stop ends in the valve handle (not shown), and an O-ring 24O to seal the knob's shaft. The upper portion 24U of bore 24B is designed to receive and mate with a SE or a HVE (not shown). Valve handle 24 is preferably made of aluminum and is about 122 mm long, overall, with other dimensions sized proportionately.

OPERATION—FIGS. 3-6

In operation, the DP turns on the vacuum at a central source (not shown) so as to create a partial vacuum (hereafter "vacuum") in hose connector 12' (FIG. 3). The DP and the patient will not hear any rushing sound because crown cap 22 seals the upper end of connector 12'.

Assume that the DP wants to connect an SE or a HVE to connector 12'. The DP removes crown cap 22 without touching it and by using only one hand (not shown) as follows: The DP places lower end 24L of valve handle 24 over finial 22F (FIG. 4) and pries off the finial. This is easy to do since cap 22 has a short mating connection with connector 12'. The DP allows cap 22 to fall away so that it will hang by tether 22T, as shown in FIG. 4A. The upper, open end of connector 12' is now free and the DP and the patient will hear a rushing sound due to air rushing into the connector.

Next the DP inserts lower end 24L into connector 12' as connector 12' rests in holder 14. The DP can also do this while still holding handle 24 with one hand (not shown) by simply pushing lower end 24L into the open upper end of connector 12'. The resultant assembly will appear as shown in FIG. 4A. The rushing sound will stop because valve knob 24K is turned to the OFF position.

Note that the DP can remove the cap and connect the valve handle by using one hand only and without touching connector 12', the hose, or the instrument holder with either hand.

Next the DP lifts the assembly of FIG. 4A off the instrument holder; the attached vacuum hose (not shown) will follow. The DP inserts the SE or HVE into open upper end 24U of handle 24, turns on the valve using knob 24K, and proceeds to use the SE or HVE to vacuum the patient's mouth (not shown) conventionally. During this procedure, the DP handles handle 24 and the SE or HVE, but not connector 12' since shoulder or skirt 24S flares outwardly and prevents the DP's hand from moving downwardly to touch the connector, in accordance with our above copending application. In other words, the DP's hand never reaches below the skirt.

If the DP needs to place the SE or HVE assembly down temporarily, the DP merely turns off valve knob 24K and replaces the assembly in instrument holder 14. At no time will the DP have to touch connector 12' or the instrument holder with either hand. Thus the DP's hand will not pick up MOs from these parts.

Assume now that the DP is finished with the patient and is ready to discard the disposable parts of the assembly, i.e., the SE or HVE, and sterilize handle 24, and replace crown cap 22. The DP turns off valve knob 24K and replaces the valve handle as shown in FIG. 4A. The DP removes the usual latex hand gloves (not shown) or washes both hands with gloves on. The DP can also wash his or her bare hands if he or she did not wear gloves. The DP's hands no longer contain MOs from the patient. The DP then removes valve handle 24 and the attached SE or HVE from connector 12' by lifting the assembly out of the instrument holder with one hand on handle 24 and then using the other hand to pull off connector 12'. The DP then replaces connector 12' in the instrument holder and reconnects crown cap 22 with the hand that did not touch handle 24. The DP now can rewash the hand that touched handle 24 to remove MOs therefrom.

FIG. 7—FLIP TOP LID SEAL

In lieu of crown cap 22 of FIG. 3 et seq., a flip-top lid or cap can be used to seal the hose connector, yet provide a seal which is removable by the valve handle without touching the seal with the DP's hand.

As shown in FIG. 7, a modified hose connector 12" contains a lower male end 12"M for mating with the vacuum hose (not shown), a body portion 12"B, shoulder 12"S, and an upper extension 12"E. At the top of shoulder 12"S are ridges 12"R similar to those of the connector of FIG. 3 to aid in gripping and prevent slipping of the DP's wet gloved hands. The open upper end of extension 12"E is sealed by a flip-top lid 12"F which is hingedly connected to one side of the extension. Lid 12"F is hinged to extension 12"E by a hinge pin 12"P which has two projecting pin portions and extends through two holes 12"H (FIG. 7E). Lid 12"F has a square shape as seen in FIG. 7C with projecting hinge pins 12"P at one side and an upturned lip 12"U on the other side to facilitate lifting up the lid by handle 24, as will be explained. Lid 12"F may have a center depression 12"D to facilitate sealing with a mating concave portion of connector 12".

Returning to connector 12", note that its upper extension 12"E has a notch, recess, or ramp 12"N to facilitate access to the underside of lid 12"F. The opposite side of extension 12"E has an indentation or recess 12"I for accommodating lid 12"F when it opened and turned down, as shown in FIG. 7B. The upper end of extension 12"E has a seat or square opening (not shown) with a concave depression to sealingly mate with lid 12"F.

OPERATION—FIGS. 7-7G

The flip-top lid embodiment of FIG. 7 et seq. can be operated with one hand in a similar manner to that of FIG. 3 et seq., except that flip-top lid 12"F is pried off connector 12" with the bottom of handle 24, rather than using such bottom to lift off the crown cap. Specifically, as shown in FIG. 7a, the DP holds handle 24 and uses its lower end 24L to pry up lid 12"F and flip it over and back as indicated by the curved arrow. The lid will then rest in indentation 12"I as indicated in FIG. 7B. The DP can then insert lower end 24L into connector 12" as indicated in FIG. 7B and then lift off the entire assembly (handle 24, connector 12", and hose 20). This can be done with one hand only, as before, thereby avoiding any soiling of the non-sterilizable parts. The DP inserts an SE or HVE tube (FIG. 7B) into handle 24 and vacuums the patient's mouth.

When the DP is finished with the patient, the same procedures as before are followed, except that instead of replacing the crown cap, the DP flips lid 12"F back after disconnecting handle 24 from the connector. Lid 12"F can be flipped back with one finger and the vacuum in connector 12"S will draw and hold it shut.

SUMMARY, RAMIFICATIONS, AND SCOPE

Accordingly the reader will see that, according to the invention, we have provided a hose connector and capping arrangement which will accomplish all of the following:

- prevent MOs from one dental patient's mouth from traveling to and entering other patients' mouths;
- reduce the spread of infectious diseases, including hepatitis and the AIDS virus, in dental environments;
- prevent cross-contamination of dental patients by MOs;
- prevent MOs from cross-contaminating patients via dental instruments, their holders, and/or the hands of dental personnel;
- avoid the need to chemically or thermally sterilize dental fluid hoses;
- prevent such cross-contamination with dental ejectors, evacuators, etc.;
- provide a viable alternative to all non-sterillizable instrument holders;
- prevent the rushing sound which occurs when a suction tube and valve or connector are removed from a vacuum hose;
- avoid the need to turn off the vacuum at its source or the hose valve during this operation;
- avoid the need to turn on the valve or source again after a new valve is installed;
- avoid any delay associated with the re-turn-on of the source;
- avoid the need to sterilize hose connector plugs and provide duplicate plugs for use while one is being sterilized;
- avoid loss of such plugs;
- avoid the need to use plastic covers and barriers to cover instruments and parts when in use;
- dental suction tubes and instruments which can be assembled with one hand and without the use of two hands, thereby to further reduce soiling of vacuum hoses with MOs from the patient's mouth; and
- provide a new, attractive, and easy-to-use cap for a vacuum hose connector.

While the above description contains many specificities, these should not be construed as limitations on the scope of the invention, but as exemplifications of the presently-preferred embodiments thereof. Many other ramifications and variations are possible within the teachings of the invention. For example, lid 12"F can be made circular, the crown cap can have other shapes, the finial can be omitted at some loss of of convenience, the finial can be replaced by a recess or indentation in the top or side of the lid, all of the other parts can be reshaped, the materials recommended can be changed, etc.

Thus the scope of the invention should be determined by the appended claims and their legal equivalents, and not by the examples given.

We claim:

1. An aseptic assembly comprising a connector and a cap, said connector being arranged to couple a vacuum instrument of the type having a male coupling with a lumen therethrough to a vacuum hose, said cap being arranged to close an open end of said connector when said vacuum instrument is not attached to said connector, said connector comprising a cylindrical member having proximal and distal ends, said proximal end being attachable to said vacuum hose, said distal end of said connector being open and comprising attachement means for attaching said connector to said vacuum instrument, said cap comprising a member shaped to seal said open distal end of said connector, said member containing removal means for enabling said cap to be removed from said connector with only said male coupling of said vacuum instrument, said removal means comprising an elongated final projecting from said top of said cap, said member being dome-shaped, cylindrical, and having a top and an open bottom, said open bottom having coupling means for coupling said cap to said distal end of said connector.

2. The assembly of claim 1 wherein:

said coupling means of said cap comprises a female mating portion, said distal end of said connector comprises a male portion for mating with said female mating portion of said cap, and said distal end of said connector contains a lumen which includes said attachement means for attaching said connector to said vacuum instrument.

3. The assembly of claim 1, further including said vacuum instrument, said vacuum instrument comprising a valved handle having a distal end which contains means for attachment to a saliva ejector.

4. The assembly of claim 1 wherein said connector has shoulder means projecting outwardly from an outside surface thereof, such that when said connector is placed in an instrument holder, said shoulder will support said connector within said instrument holder.

5. An aseptic assembly comprising a connector, a cap, and a vacuum instrument having a male coupling with a lumen therethrough, said connector being arranged to couple said vacuum instrument to a vacuum hose, said cap being arranged to close an open end of said connector when said vacuum instrument is not attached to said connector, said connector comprising a cylindrical member having proximal and distal ends, said proximal end being attachable to said vacuum hose, said distal end of said connector being open and comprising attachment means for attaching said connector to said vacuum instrument, said cap comprising a dome-shaped, cylindrical member, said dome-shaped, cylindrical member having an open bottom with coupling means for coupling said cap to said distal end of said connector, said coupling means shaped to seal said open distal end of said connector, said cap contianing removal means for enabling said cap to be removed from said connector with only said male coupling of said vacuum instrument, said removal means of said cap comprising a top which has an elongated finial projecting therefrom, said vacuum instrument comprising a valved handle having a distal end which contains means for attachment to a saliva ejector.

6. An aseptic assembly comprising a connector and a cap, said connector comprising a cylindrical member having proximal and distal ends, said proximal end being sealingly attachable to an end of a vacuum hose, said distal end being open and comprising attachment means for attaching said connector to a vacuum instrument of the type having a male coupling with a lumen therethrough, said cap comprising a dome-shaped, cylindrical member shaped to seal said open distal end of said connector when said vacuum instrument is not attached thereto, said dome-shaped, cylindrical member having a top and an open bottom with coupling means for coupling said cap to said distal end of said connector, said cap containing removal means for enabling said cap to be removed from said connector with only said male coupling of said vacuum instrument, said removal means comprising an elongated finial projecting from said top, whereby said connector will enable said vacuum instrument to be connected to said vacuum hose and said cap will be able to seal said connector and hence said hose when said vacuum instrument is not connected to said connector.

7. The combination of claim 6, further including said vacuum instrument, said vacuum instrument comprising a valved handle having a distal end which contains means for attachment to a saliva ejector.

* * * * *